United States Patent [19]

Kimura et al.

US005776756A

[11] Patent Number: 5,776,756
[45] Date of Patent: Jul. 7, 1998

[54] FERMENTATION COMPOSITIONS HAVING SUPEROXIDE DISMUTATING ACTIVITY AND AN ANTIHYPERTENSIVE AGENT FOR TREATMENT OF CONSTIPATION EACH HAVING THE SUPEROXIDE DISMUTATING ACTIVITY

[75] Inventors: Akihiko Kimura; Atsushi Takada; Naoto Ishikawa, all of Aichi, Japan

[73] Assignee: Toyo Hakko Co., Ltd., Obu, Japan

[21] Appl. No.: 522,150

[22] Filed: Aug. 31, 1995

[51] Int. Cl.$^6$ .............................. C12N 9/02; A01N 43/08
[52] U.S. Cl. ..................... 435/189; 435/41; 424/195.1; 514/474
[58] Field of Search ............... 435/189, 41; 424/195.1; 514/474

[56] References Cited

FOREIGN PATENT DOCUMENTS

| | | |
|---|---|---|
| 63-79834 | 4/1988 | Japan . |
| 2-154622 | 6/1990 | Japan . |

OTHER PUBLICATIONS

Active Oxygen—Molecular Mechanism of the Formation, Bleaching and Function in Living Bodies, the new and second edition, edited by Minoru Nakano et al., and published by Kyoritsu Pub. Co., Ltd., p. 64, and pp. 223–230.

*Primary Examiner*—Leon B. Lankford, Jr.
*Attorney, Agent, or Firm*—Morgan, Lewis & Bockius LLP

[57] ABSTRACT

The present invention provides a fermentation composition which makes use of rice brans, soybeans and sources of carbon as starting materials and which is innoxious, has a good SOD action (the action of effectively eliminating $O_2^-$ which is harmful to the living body and the action of preventing diseases), and can prevent degradation of vitamin C. The invention also relates to an antihypertensive agent and constipation improver which are innoxious and have a good SOD action. The fermentation composition comprises a fermentation liquid obtained by inoculating and cultivating, under aerating and agitating conditions, bacillus natto or grass bacilli in a liquid medium,a pH of the medium is controled in the range of from 7.5 to 10 by alkaline agents, containing a rice bran, a soybean, a source of carbon and water, and filtering the resultant cultivation broth, or an evaporation residue of the fermentation liquid, vitamin C and, optionally, an extract of green tea or its evaporation residue.

16 Claims, 2 Drawing Sheets

FERMENTATION COMPOSITIONS HAVING SUPEROXIDE DISMUTATING ACTIVITY AND AN ANTIHYPERTENSIVE AGENT FOR TREATMENT OF CONSTIPATION EACH HAVING THE SUPEROXIDE DISMUTATING ACTIVITY

BACKGROUND OF THE INVENTION

The present invention provides a fermentation compositions which have a good SOD action and more particularly, to fermentation compositions which comprises, at least, a specific type of fermented liquid and vitamin C. The other invention relates to an antihypertensive agent and an improver for constipation which also have a good SOD action. The compositions of the present invention have wide utility in the fields of treatment and improvement such as of various types of diseases caused by active oxygen ($O_2^-$) including diseases caused by bloodstream troubles such as myocardial infarction, cerebral apoploxy,hypertension, menstrul pain, the stiffness of the shoulders, nerve pain, lambagos, crapulence and the like, adult and internal diseases such as cancer, nephritis, hepatitis,diabetes and the like, and beauty cares and dermatoses such as spots, epherides, skin chapping, anematosis, constipation, wrinkles, atopic dermatitis and the like.

Superoxide dismutase (SOD) is an enzyme which is a catalyst for an inhomogeneous reaction of the following formula of the superoxide radical formed by reduction of an oxygen molecule with one electron at a rate close to that in a diffusion rate determining step thereby lowering the concentration of $O_2^-$ in the cells $$O_2^{31}+O_2^-+2H^+ \rightarrow H_2O_2-O_2$$

If $O_2^-$ is harmful to the living body, SOD which is an enzyme for eliminating $O_2^-$ is considered to exist in order to protect the living body from thetoxicity of the active oxygen, so that SOD is useful in treating diseases considered to result from the active oxygen. From this standpoint, studies have been recently made on the reaction mechanism and the physiological mechanism of the SOD ("Active Oxygen—Molecular Mechanism of the Formation, Bleaching and Function in Living Bodies", the new and second edition, edited by Minoru NAKANO et al., and published by Kyoritsu Pub. Co., Ltd., p. 223 to 230).

It is known that the SOD activity is low in cancer cells. Although the direct causal relation between the SOD and the carcinogenesis has not been clearly elucidated, it has been reported that when injected into cancer cells, SOD and SOD analogues inhibit proliferation (the above "Active Oxygen", p. 64).

If a fermentation composition such as for foods is provided as being innoxious and having the SOD action (the term "SOD action" used herein means not only the action of reducing the active oxygen concentration, but also the action of preventing and improving various types of diseases caused thereby), it is very useful for human health and beauty cares, with a very great demand therefor. Especially, under recent circumstances where one suffers from a great stress and a variety of diseases, such a demand would be serious.

On the other hand, it is known that vitamin C in the form of an aqueous solution is not stable and readily degrades. Thus, the effect of vitamin C cannot be shown satisfactorily over a long time, with the attendant problem that it has to be added to foods in larger amounts than as required.

SUMMARY OF THE INVENTION

An object of the invention is to provide a fermentation composition which is prepared from rice brans, soybeans and sources of carbon and is safe to the health and has a good SOD action and which can prevent vitamin C from degradation when used in combination.

We made intensive and extensive studies on innoxious fermented products having the SOD activity and also on how to prevent degradable vitamin C from degradation. As a result, it has been found that when a fermentation liquid which is obtained by fermenting the above-mentioned starting materials and filtering the resultant fermented product is formulated, at least, with vitamin C, the above object can be achieved. The invention is based on this finding.

The fermentation composition having a good SOD action according to a first embodiment of the invention is characterized by comprising a fermentation liquid, or an evaporation residue of the liquid, obtained by inoculating Bacillus natto or hay or grass bacilli (Bacillus substilis) in a medium containing rice brans, soybeans, sources of carbon and water, cultivating the bacilli and filtering the resultant broth, and vitamin C. According to a second embodiment of the invention, there is also provided a fermentation composition which comprises a fermentation liquid, or an evaporation residue thereof, obtained by inoculating Bacillus natto or hay or grass bacilli (Bacillus substilis) in a medium containing rice brans, soybeans , sources of carbon and water, cultivating the bacilli and filtering the resultant broth, vitamin C, and an extract of green tea or an evaporation residue of the extract.

According to a third embodiment of the invention, there is provided a fermentation composition which comprises a fermentation liquid, or an evaporation residue of the liquid, obtained by inoculating Bacillus natto or hay or grass bacilli (Bacillus substilis) in a medium containing rice brans, soybeans, sources of carbon and water, cultivating the bacilli and filtering the resultant broth, and an extract of green tea or an evaporation residue of the extract.

The fermentation compositions of the invention have a good SOD action and thus exhibit a good effect based on the SOID action (e .g. an antihypertensive effect). Accordingly, the compositions of the invention are considered to show good effects of curing and improving various diseases caused by active oxygen, e.g. diseases caused by bloodstream troubles such as myocardinal infarction, cerebral apoploxy, hypertension, menstrul pain, the stiffness of the shoulders, nerve pain, lambagos, crapulence and the like, adult and internal diseases such as cancer, nephritis, hepatitis, diabetes and the like, and beauty cares and dermatoses such as spots, epherides, skin chapping, anematosis, wrinkles, atopic dermatitis and the like.

With the composition of the invention which contains vitamin C, the vitamin C present in the composition is prevented from degradation, ensuring an efficient use of vitamin C.

Moreover, with a water-soluble fermentation composition, the effect of absorption is good and the composition has wide utility as foods and the like.

Since the fermentation liquid used in the present invention consists of a natural fermented product derived from fully natural starting materials, it is substantially free of any harmful bacilli or germs and heavy metals and is in safety to the health. In addition, rice bran and soybean products which are useful for improving the health and beauty are used as the starting materials and contain useful nitrogen compounds (amino acids and the like), ash, phosphorus compounds and the like, the fermentation compositions are well-balanced. Further, the extract of green tea is derived from the natural product, and fermentation compositions comprising the extract are of no safety problem.

In the invention, under aerating and agitating conditions, homogeneous and effective fermentation is conducted in the alkaline state medium, normally only a poor fermentation is occurred in the medium. Moreover, with a liquid cultivation, different from a solid cultivation, the pollution of the fermentation liquid by baccili or germs is prevented. Thus, the fermentation liquid is suitable for foods and the like.

Another object of the invention is to provide an antihypertensive agent and improver for constipation (which may hereinafter generically be referred to as antihypertensive agent etc.) which are derived from rice brans, soybeans and sources of carbon as starting materials and which are safe to the health and have a good SOD action.

From the above standpoint, we have made intensive and extensive studies on innoxious fermented products for use as antihypertensive agents. As a result, it has been found that the above object can be attained by formulating a fermentation liquid obtained by fermenting the afore-mentioned starting material and filtering the resulting product along with certain types of additives (e.g. an extract of green tea or an evaporation residue thereof, an oligosaccharide and the like). The invention is accomplished based on this finding.

The antihypertensive agent etc. have a good SOD action and exhibit a good effect caused by the SOO action. Accordingly, the antihypertensive agent and the improver for constipation according to the invention have, respectively, a good effect of inhibiting the blood pressure and a good effect on digestion.

When the antihypertensive agent etc. are of the water-soluble type, they are readily absorbable and will have wide utility in the fields of foods and the like.

Since the fermentation liquid used in the present invention consists of a natural fermented product derived from fully natural starting materials, it is substantially free of any harmful bacilli and heavy metals and is safe. In addition, rice bran and soybean products which are useful for improving the health and beauty are used as the starting materials and contain useful nitrogen compounds (amino acids and the like), ash, phosphorus compounds and the like, the improvers are well-balanced. Further, the extract from green tea is derived from the natural product, and the improvers comprising the extract arc of no safety problem.

DETAILED DESCRIPTION OF THE INVENTION

Figure 1:
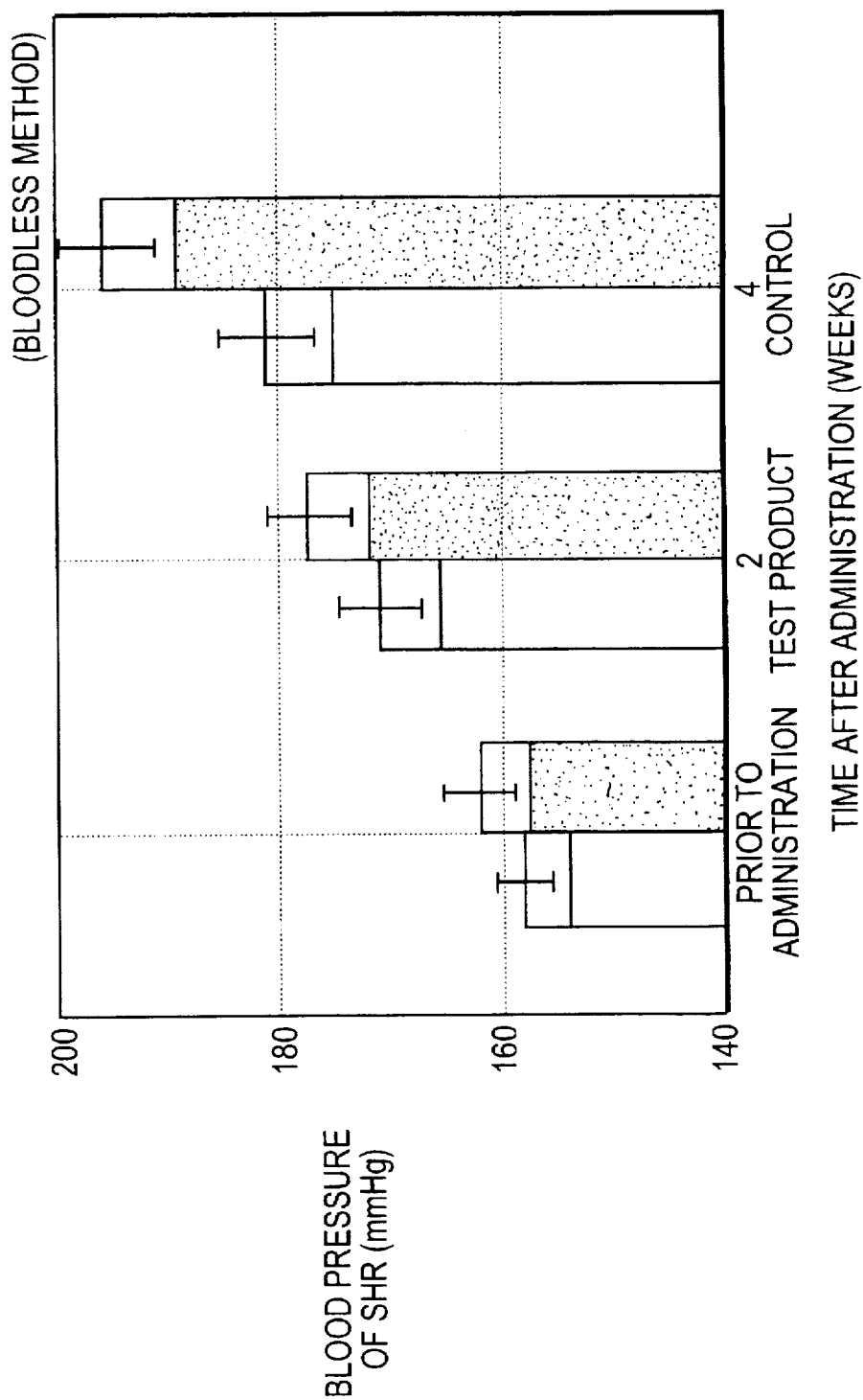
FIG. 1 is a graph showing a variation in blood pressure at a rising stage of blood pressure of SHR (spontaneous hypertensive rat) in relation to a variation in time after administration.

In the practice of the invention, the term "rice brans" is intended to mean rice germ, defatted rice germ, rice bran and defatted rice bran. The term "soybeans" means defatted soybean, soybean flour, soybean cake and hydrolysates thereof. In general, the mixing ratio is in the range of from 1 to 20 parts by weight, preferably from 10 to 20 parts by weight, of the soybeans per 100 parts by weight of the rice brans. The term "sources of carbon" means one or more carbohydrates selected from glucose, dextrin, lactose, starch and so on. The sources of carbon is formulated in an amount of from 20 to 80 parts by weight, preferably 40 to 60 parts by weight, per 100 parts by weight of the rice brans. The soybeans and the sorces of carbon are nutlient for baccili, above-mentiond amounts of them are most preferable for the developement of baccili. The medium is alkaline state by using an alkaline agent, e.g. sodium bicarbonate and the like and phytic acid, preferably in the form of its sodium salt or calcium salt, and phosphate may further be added to the medium. The phytic acid is a piJ regulator and an auxiliary agent for fermentation.

The fermentation conditions include a piJ of 7.5 to 10, preferably 8 to 10, more preferably 8.5 to 9.5, and a cultivation temperature of about 40° to 45° C. Protease may be used as a starting material for the medium. In this case, soybean peptides can be further decomposed. Thus, the protease is useful.

The term "fermentation liquid" means a liquid which is obtained after filtration of a cultivation broth, or a liquid obtained by subjecting the filtered liquid to after-treatments such as decoloration, or a concentrate thereof. As a matter of course, the evaporation residue (solid matter) of the extract may also be used.

The term "vitamin C" means one which is known as ascorbic acid and may be either an extract from natural products or one which is prepared. The vitamin C, on calculation of its solid matter, should be formulated in an amount of from 1 to 30 parts by weight, preferably from 5 to 20 parts by weight, more preferrably from 10 to 17 parts by weight, per 100 parts by weight of the evaporation residue of the fermentation liquid. If the amount is less than 1 part by weight, a satisfactory effect cannot be expected. On the other hand, if the amount exceeds 30 parts by weight, it will become too sour to take it as a drink.

The term "extract of green tea" means one which is extracted of tea leaves with a solvent such as methanol, ethanol, ethyl acetate or the like (preferably methanol or ethanol). The concentration of the extracted component should preferably be in the range of approximately from 5 to 50 wt%. The amount of the green tea extract is in the range of from 1 to 50 parts by weight, preferably from 1 to 30 parts by weight, more preferrably from 4 to 25 parts by weight, per 100 parts by weight of the evaporation residue of the fermentation liquid. If the amount is less than 1 part by weight, a satisfactory effect cannot he expected. On the other hand, if the amount exceeds 50 parts by weight, it will become difficult to take it as a drink in the sense of taste. The green tea extract can be made water-soluble by extraction with ethanol, water or a mixture of ethanol and water.

The term "oligosaccharide" means one which is a sort of saccharide, and the number of polmerized monosaccharide is from 2 to 10 or more (e.g. sucrose, raffinose, stachyose, trehalose). The amount of the oligosaccharide is in the range of from 1 to 100 parts by weight, preferably from 5 to 70 parts by weight, more preferrably from 10 to 50 parts by weight, per 100 parts by weight of the evaporation residue of the fermentation liquid. If the amount is less than 1 part by weight, a satisfactory effect cannot be expected. On the other hand, if the amount exceeds 100 parts by weight, a satisfactory effect can not he expected.

The invention is more particularly described by way of examples.

EXAMPLE 1

(1) Preparation of a Fermentation Liquid and Preparation of Test Samples for Fermentation Composition A fermentation liquid was prepared according to the following procedure.

30 kg of defatted rice bran, 3 kg of soybean cake, 15 kg of glucose, 45 kg of sodium bicarbonate, 2.5 kg of diammonium hydrogenephoshate, 5 kg of bittern and 500 kg of water were provided as a medium with a pli of approximately 9.

In the present Examples, each above-stated amount of defatted rice bran, soybean cake, glucose, sodium bicarbonate, bittern and diammonium hydrogenphoshate are added, in order and slowly, into the above-stated amount of water in fermentation drum (about 1 m$^3$ of content volume) mixing them and fermentation is prepared. The above-stated pH is prepared by adding powder of sodium bicarbonate and water solution of sodium bicarbonate slowly.

The medium prepared by the above-staled method was sterilized at 121° C. for 30 minutes and cooled, followed by inoculation of 0.05 kg of a strain of *Bacillus natto* (commercially available from Naruse Fermentation Chem. Lab.) and liquid cultivation at 40° to 45° C. for about 48 hours under aerating and agitating conditions.

The medium should contain the alkaline protease, for example "PROLETHER" and "PROTEASE P" (commercially available from Amano Pharmaceutical Co., Ltd.). In this case, soybean peptides can be further decomposed. Thus, the alkaline protease is useful. The amount of the protease is normally under 0.1 wt %, preferably 0.02 to 0.05 wt %, per 100 wt % of the total fermentation product (a mixture containing water).

The resultant culture broth was expressed and filtered, followed by treatment with active carbon and perlite for deodoration and decoloration, thereby obtaining a substantially transparent fermentation liquid (i.e. fermentation extract). The above-stated expression and filteration are done by including filter cloth in the middle, by what is called filter press. A pressure of filter press is 550 kg / 60×60 cm$^2$. The above-stated treatment with active carbon and prelite is done by injecting 600 kg of the above-stated filtrate into a tank (about 1 ton of content amount) adding 1 kg of active carbon and 1 kg of perlile, and mixing them. Thereafter by filtering the liquid treated by above-stated method, a substantially transparent fermentation liquid is obtained.

For preparation of medium, mean grain size under 1 mm of powder is used as defatted rice bran and solid of form like a pressed board broked to pieces is used by soybean cake. And powders of glucose, diammonium hydrogen phoshate, bitter and sodium bicarbonate are used. The active carbon usable for this purpose may be powdery active carbon (active carbon S, active carbon K and the like) and granular active carbon (active carbon SG and the like). The perlite used was "Perlite No. 4180" available from Daikaline Orient Co., Ltd.

The fermentation liquid was a transparent liquid which was colorless or light yellow in color and had a flavor of fermentation, with a water content of 92 to 94 % (when determined by a normal pressure heat drying procedure).

On examination, the liquid was found to be free of any ordinary live bacteria, colibacilli, molds, enzymes, arsenic and heavy metals.

An extract from green tea used in this example was a ethanol or water extract which had a solid content of 47 to 48 wt % and a concentration of ethanol and glycerin (mainly composed of ethanol) of about 50 wt % with a water content of about 2.6 wt % and a specific gravity of 1.07 to 1.09. It will be noted that the solid content was determined as a Brix value. Vitamin C (L-ascorbic acid) used was a powder product having a purity of not less than 99%.

(2) Test on the SOD Action The fermentation liquid, green tea extract and vitamin C were formulated at ratios indicated below to prepare sample Nos. A to G.

| No. A | fermentation liquid | 100 g |
|---|---|---|
| No. B | green tea extract | 1 g |
|  | purified water | 99 g |
| No. C | vitamin C | 1 g |
|  | purified water | 99 g |
| No. D | vitamin C | 1 g |
|  | green tea extract | 1 g |
|  | purified water | 99 g |
| No. E | fermentation liquid | 99 g |
|  | green tea extract | 1 g |
| No. F | fermentation liquid | 99 g |
|  | vitamin C | 1 g |
| No. G | fermentation liquid | 98 g |
|  | vitamin C | 1 g |
|  | green tea extract | 1 g |

It will be noted that in No. G, the ratios by weight of the solid matters in the respective components were such that fermentation liquid: vitamin C: green tea extract= 100:14.6:7.0.

(2) Measurement of SOD Activity

The respective samples were subjected to measurement of the SOD activity according to the following measuring method, with the results shown in Table 1.

(Measuring Method for SOD Activity)

This method makes use of an EPR (electron paramagnetic resonance) apparatus and has been recently added to test items of the Japanese Food Analyzing Center as "Superoxide Subtractive Activity". More particularly, 1 g of each homogenized sample was admixed with a 0.1M phosphate buffer solution (pH 7.8), followed by sufficient extraction to obtain an extract. Thereafter, the following reagents were further mixed with the extract.

2 mM hypoxanthine/phosphate buffer solution: 50μl 5.5 mM DETAPAC (diethylenetriaminepentaacetic acid/ phosphate buffer solution: 35 μl Extract or reference SOD (superoxide dismutase: 50 μl DMPO (5.5-dimethyl-1-pyrroline-1-oxide): 15 μl 0.4 units/ml xanthine oxidase/phosphate buffer solution: 50 μl Subsequently, the resultant mixture was sucked up in a specific flat cell (with a capacity of about 130 μl, commercially available from JEUL Ltd.) and set on an ESR device (Model JES-FR80, commercially available from JEOL Ltd.) After 40 seconds, scanning was commenced, followed by measurement under the following ESR operating conditions. It will be noted that the SOD activity was measured with respect to a solution one day after the preparation of the sample.

(ESR operating conditions)

| Temperature | room temperature |
|---|---|
| Microwave output | 8 mW |
| Magnetic field | 334.7 mT ± 5 mT |
| Modulation | 100 kHz, 0.79 × 0.1 mT |
| Amplification rate | 3.2 × 100 |
| Response time | 0.1 second |
| Scanning time | 2 minutes |

The ratio between the height of peak of Mn2+ and the height of peak of a measured signal was determined. Subsequently, the calibration curve of a reference SUD (0 to 15 units/ml) was made. The value obtained using each extract was interpolated, from which a subtractive activity of the sample was calculated. The results are shown in Table 1. It will be noted that the "SOD activity average theoretical value" is one which is determined using the SOD activity values (a values) of sample Nos. A, B and C.

TABLE 1

| Sample No. | SOD Activity (a) | SOD activity average theoretical value (b) | ratio of (a/b) |
|---|---|---|---|
| A | 3.965 | — | — |
| B | 0.660 | — | — |
| C | 3.800 | — | — |
| D | 4.400 | 4.460 | 0.987 |
| E | 5.300 | 4.590 | 1.15 |
| F | 9.100 | 7.730 | 1.18 |
| G | 9.800 | 8.350 | 1.17 |

(3) Test results

As shown in Table 1, with sample No. D (green tea extract + vitamin C), the theoretical value (value of B in Table 1) is substantially equal to the measurement (value of a in Table 1) (1:0.987), revealing a mere additive effect. On the other hand, where the fermentation liquid is mixed (Nos. E, to G), the ratios of A and B are, respectively, 1.15, 1.18 and 1.17, all of these samples exhibiting a significant synergistic effect. More particularly, the sample No. F (fermentation liquid + vitamin C) had a ratio of a and b of 1.18. Likewise, the sample No. G (fermentation liquid + vitamin C and green tea extract) had a ratio of 1.17. In both samples, a good synergistic effect was recognized. It will he noted that a similar good synergistic effect is shown for the sample No. E (fermentation liquid + green tea extract) which is free of vitamin C (the ratio being 1.15).

It has been generally accepted that those having a good SOD activity are unstable in the form of an aqueous solution. Especially, the aqueous solution of vitamin C lowers in activity. In this sense, the aqueous solutions of the sample Nos. B, C and D may not be stable.

In this measurement of the SOD activity, the solutions one day after the preparation of the samples were used for the measurement of the activity. Accordingly, it is considered that the SOD activities of the sample solutions will be lower than those as would he developed immediately after the preparation. FIrom this, it can be assumed that when mixed with the fermentation liquid, vitamin C and the green tea extract are able to develop the SOD activity as being fresh even after the passage of time.

The compositions of the samples were found to be free of any harmful germs and heavy metals in the respective components. Especially, the fermentation liquid is safe to the health since it is a naturally fermented product of natural starting materials. As will be apparent from the results of the table, the tested compositions are excellent in the SOD action and are considered to have good effects, such as an antihypertensive effect, caused by the SOD action.

The fermentation liquid, green tea extract and vitamin C are all soluble in water and can be used as aqueous drinks, foods and the like after dissolution in water, thus being excellent in absorption in body.

EXAMPLE 2

(1) Preparation of Test Products Having Compositions for SOD Test

The SOD action of the fermentation composition in the invention was further evaluated. As test product 1, there was used a composition which was comprised of 100 parts by weight of the fermentation liquid obtained above and 3 parts by weight of a green tea extract (methanol or ethanol extract with a solid content of 47 to 48 wt % and a specific gravity of 1.07 to 1.09). The composition had an evaporation residue ratio between the residue from the fermentation liquid and that from the extract of 100:20. It will be noted that the solid content was determined as a Brix value with a concentration of ethanol and glycerin (mainly composed of ethanol) being about 50 wt % and a concentration of water of about 2.6 wt %.

(2) Evaluation of Characteristic Properties
(A) SOD Action

Under the following conditions, the sample was subjected to a test for $H_2O_2$ (Tables 2 and 3), a test for OH (Table 4) and a test for $O_2$-xanthine system (Table 5). The results are shown in the respective tables. The test sample was a 1:5 dilution of the test product 1 with water.

TABLE 2

| | $H_2O_2$ | | | |
|---|---|---|---|---|
| Test 1 | 0 min. | 10 min. | average/min. | PLCO mols/min. |
| Control | 5 | 50 | 2.2 | 348 |
| Test product 1 | 75 | 73 | 0.2 | 28 |

TABLE 3

| | $H_2O_2$ | | | |
|---|---|---|---|---|
| Test 2 | 0 min. | 10 min. | average/min. | PLCO mols/min. |
| Control | 75 | 23 | 5.2 | 723 |
| Test product 1 | 75 | 70 | 0.5 | 70 |

TABLE 4

| | OH | |
|---|---|---|
| | Test 1 | Test 2 |
| Stimulater/incubation | 40 min. | 40 min. |
| Control | 174.8 | 12.49 |
| Test product 1 | 153.0 | 1.87 |

TABLE 5

| | $O_2$-xanthine system | | |
|---|---|---|---|
| | O.D. (nM) | | |
| Sample | C (2 min.–1 min.) | C-black | nM/min |
| Control | | 0.0251 | 1.190 |
| Test product 1 | 0.0244 | 0.0205 | 0.972 |

As shown in Tables 2 to 5, the test product 1 of the invention is better in the SOD action than the control. From the above results, the SOD activity is found to be 460 units/ml (10 ml for one cup).

The examples should not he construed as limiting the invention thereto, but various variations and modifications depending on the purpose and application may be possible within the scope of the invention. For instance, the fermentation compositions are ordinarily in the form of a liquid such as an aqueous solution or stock solution as shown in the examples, powers, granules, tablets formulated with other types of power components (fillers) or microcapsules, soft capsules, hard capsules, candies, jellies, biscuits and the like may be used wherein the fermentation liquid impregnated in absorptive powder especially for the powders, granules and tablets. Moreover, these aqueous solutions, powders and the like may be filled in a given container. Alternatively, the aqueous solutions, powders and the like may be used as it is or in combination with other agents (whichever an aqueous solution, an oil or a powder) without limitation. For instance, the composition of the invention may be of the potion type, or may be filled in a container of a desired form. With powders, they may be filled in a stick-shaped container or pouch or may be formulated or dispersed in ordinary refreshing drinks, other drinks, milk products, oil products and the like. The dispersion may be ether of the oil-in-water type or the water-in-oil type. In addition, the composition may be formulated with other nutrient ingredients such as, for example, various types of vitamins, calcium ion component, iron ion component and the like, medical ingredients, seasoning ingredients, flavoring ingredients and the like. Of these, water-soluble ingredients or components are preferred. This is because a uniformly dissolved solution can be provided as a commercial product.

EXAMPLE 3

(1) Preparation of a Test Product for Antihypertensive Agents (A) Variation in Blood Pressure at a Blood Pressure Rising Stage of Rats 100 parts by weight of the fermentation liquid used in the foregoing examples was formulated with 1.5 parts by weight of the green tea extract used before to provide test product 2. The product was administered under the following conditions to assess a variation of blood pressure. The results are shown in FIG. 1.

(Test conditions)

(1) Test animals were three male rats for control and four male rats for test and thus consisted of seven rats in total. These rats were each six weeks old and had a blood pressure not lower than 150 mmHg. The rats used had such a genetic nature that the blood pressure increased from the three weeks in age (hereinafter referred to simply as SHR).

(2) Manner of test administration: free intake from a water supply bottle.

(3) Test room: temperature 23±1° C. and humidity of 50%±10%.

(4) Drink: for easy drink, glucose and citric acid were added to a solution of 10% test product 2 (having the SOD activity).

(5) Measurement of blood pressure: one measurement per two weeks.

(6) Feed used: a common feed "MF" available from Oriental Yeast CO., Ltd., was used.

The results reveal that the test product 2 is better in suppressing the blood pressure rise than the control.

(B) Variation in Blood Pressure at a Hypertension Complete Stage of Rats

The variation of the blood pressure by administration of the test product 2 was evaluated under the same conditions as in (A) except the following conditions. The results are shown in FIG. 2.

(Test conditions)

(1) Animals used consisted of four male rats (SHR) for control and four male rates for test product, thus being eight in total. The rats were 12 to 15 weeks old in age, with the blood pressure being not lower than 180 mmHg. Other conditions were the same as in (A).

Figure 2:
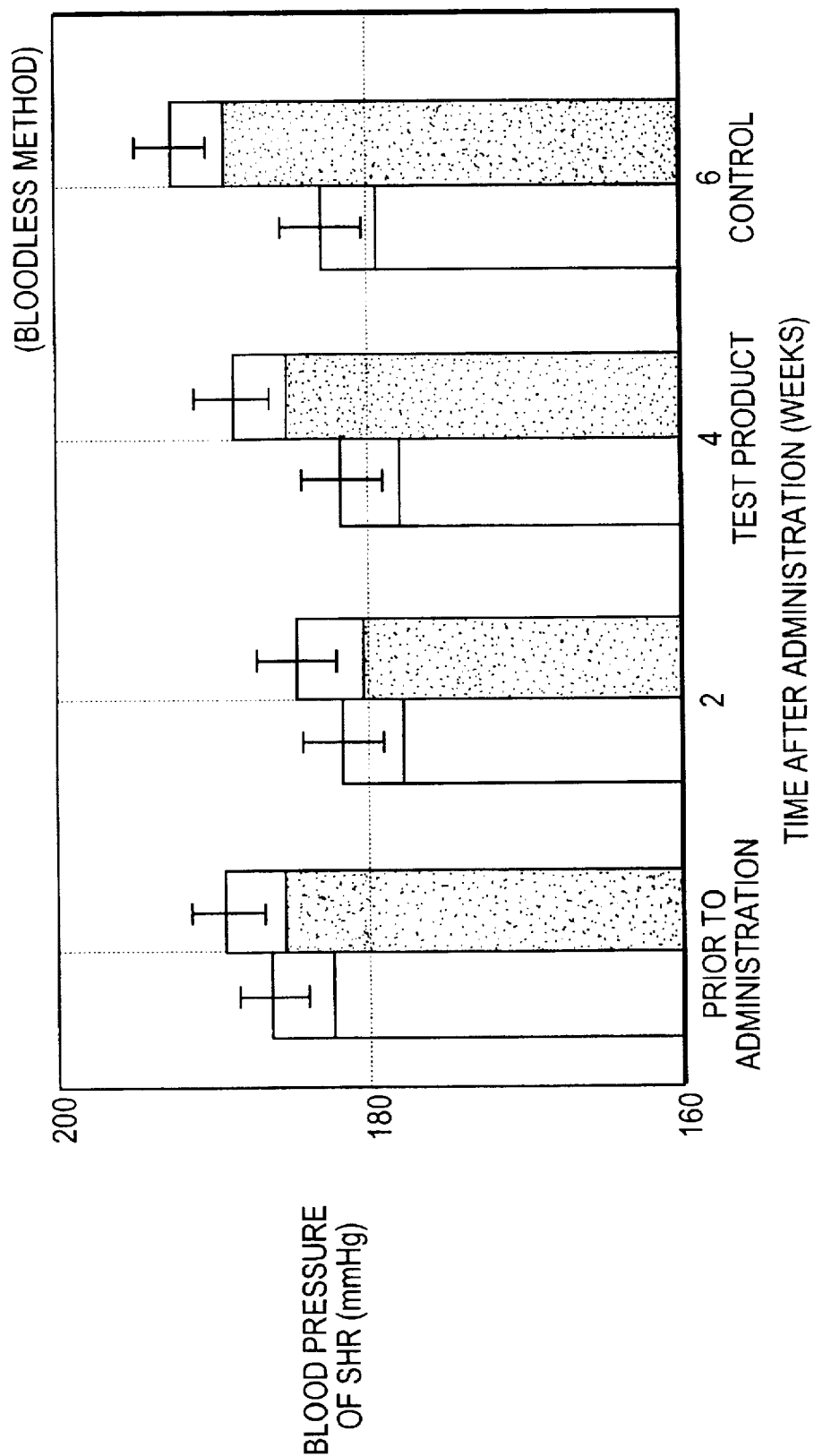
FIG. 2 is a graph showing a variation in blood pressure at a hypertension complete stage of SHR in relation to a variation in time after administration.

The results of FIG. 2 show that the test product has an effect of suppressing the hypertension and also has a good effect of the suppression as the time after the administration passes.

(C) Monitor Test (1) A monitor test was carried out with respect to the improving effect of constipation in the following manner, with the following good results. The test was made such that (i) 50 constipated women (effective answerers being 49 in number) were tested and (ii) 5 ml of a stock solution (fermentation liquid) was taken within 30 minutes after rising. As a result, it was found that 38 women had a movement at the first day and 49 women had all a passage at the second and third days.

(2) Then, a test product (potion of 10 ml) was prepared as consisting of 60 parts by weight of the fermentation liquid, 1.2 parts by weight of the green tea extract, 14 parts by weight of oligosaccharide and the balance of purified water. The potion was subjected to a clinical monitor test, with the following good results.

(1) A (58 years old woman)

(Symptom prior to the commencement of the monitor test).

The woman became dark-complexioned in the face and felt very hard to go up and down the stairs. The blood pressure was as high as 165 and she took an antihypertensive agent daily.

(Results after taking two potions every day) She could step lightly after about one week. Then, the agent was stopped from taking and the blood pressure was down to as low as 130 in about three weeks. In two months, she was so improved in appearance as to look younger by 10 years in age than before and had a fair face.

(2) B ( 70 years old man) (Symptom prior to the commencement of the monitor test).

He had a trouble with cardiopulmonary function. In every day life, when going up the stairs, he was short of breath and walked as dragging feet.

(Results after taking three potions (morning, noon, and night) every day) In approximately two weeks, he started to feel himself comfortable. In approximately one month, he had a long wind on ascending the stairs. After four months, when the cardiopulmonary function was checked in the hospital, he was improved. In this winter season, he did not catch cold for the first time and was good in health without necessity of hospital treatment.

(3) C (53 years old woman)

(Symptom prior to the commencement of the monitor test) She was hypertensive and had diabetic and costive troubles. The blood pressure was 180 over 95.

(Results after taking two potions every day over two months and thereafter one potion everyday). At the fourth day after the administration, the urinary output was doubled and thus, she was improved in health. She had a bowel motion every three days and then every two days. After two months, the doctor indicated that she had no necessity of taking the antihypertensive agent The blood pressure was 145 over 78, under which the drug was not necessary.

(4) D (23 years old woman) (Symptom prior to the commencement of the monitor test).

She suffered from hard constipation from an infant and had only one movement in ten days to two weeks. The rash always came out in fine spots on her face, with her skin being rough. Although she was relatively slender in figure, her abdominal region was in the form of a potbelly like the figure of an infant, with which she was annoyed.

(Results after taking five potions over the first two days and subsequently two potions everyday)

She had a movement in the morning of the second day and thereafter, had regular movements. After one and a half months, she had no rash on the face with her skin being bright.

(5) E (70 years old woman)

(Symptom prior to the commencement of the monitor test)

She was hypertensive with her blood pressure of 200 and thus entered a hospital.

(Results after taking two potions (in the morning and night) everyday)

The blood pressure descended in ten days and she could leave the hospital. At present, the blood pressure was 140.

(6) V (68 years old woman)

(Symptom prior to the commencement of the monitor test)

She was tired out, and felt languid and tightened up in body.

(Results after taking two potions (in the morning and night) everyday)

At the second day, she was improved in skin as being wet and cosmetics spread well on the face. After the two weeks, she recovered from her fatigue, so that she felt tireless and could move as desired.

(7) G (45 years old man)

(Symptom prior to the commencement of the monitor test)

He suffered from diabetes and often repeated hospitalization over two to three weeks at a time. During the course of the treatment, he had a liver trouble.

(Results after taking two potions everyday)

After two months, the doctor indicated that the liver was fully cured. After four months, the diabetes was so cured that he began to work and could return to active life. Thereafter, no hospitalization became necessary.

(D) Summary of the Effects in Examples

As set out hereinbefore, the fermentation liquid of the invention is free of any harmful germs or bacilli and heavy metals and is a natural fermented product obtained from fully natural starting materials and is safe to the health. As will be apparent from the results of the examples, the liquid has a good SOD action and can thus exhibit such a good antihypertensive effect as set out hereinbefore. Since the liquid has the good SOD action, similar effects other than the antihypertensive effect and caused by the SOD action will be expected.

We believe that the fermentation liquid has the action of effectively taking an extract from green tea in the body. In this regard, further detailed studies will be necessary. Nevertheless, it has been found that the combination of the fermentation liquid and vitamin C, optionaly the green tea extract contributes to further improvement of the SOD action. In addition, one can reliably drink such a combination and is very useful to the human body with respect to the health and beauty.

Both fermentation liquid and green tea extract are soluble in water. As set forth in the foregoing tests, both ingredients can be used as water-soluble drinks or foods after dissolution in water, ensuring good absorption in body. Moreover, as shown in the monitor test of (C), the test product (in the form of an aqueous solution) is placed in a potion-type container and provided as drink (food) for the test. Thus, the fermentation liquid can be readily provided as various types of commercial products in the form of an aqueous solution such as drinks or drinking agents.

What is claimed is:

1. A composition having superoxide dismutating activity comprising:
   (a) vitamin C; and
   (b) a fermentation composition, wherein said fermentation composition is obtained by:
      (1) inoculating a microorganism on a culture medium, wherein said microorganism is selected from the group consisting of *Bacillus natto* and *Bacillus subtilis*;
      (2) cultivating said inoculated microorganism, under aerating and agitating conditions, in a fermentation liquid medium, wherein said medium comprises rice bran, soybean, carbon, and water, and wherein the pH of the medium is about 7.5 to about 10; and
      (3) filtering the resultant cultivation broth, or an evaporation residue of said fermentation liquid, to obtain the fermentation composition.

2. The composition of claim 1, wherein said vitamin C is present in an amount of from about 1 to about 30 parts by weight, calculated as a solid content, per 100 parts by weight of the evaporation residue of said fermentation liquid.

3. The composition of claim 2, wherein said vitamin C is present in an amount of from about 10 to about 17 parts by weight, calculated as a solid content, per 100 parts by weight of the evaporation residue of said fermentation liquid.

4. A composition having superoxide dismutating activity comprising:
   (a) vitamin C;
   (b) an extract of green tea or an evaporation residue of said green tea extract; and
   (c) a fermentation composition, wherein said fermentation composition is obtained by:
      (1) inoculating a microorganism on a culture medium, wherein said microorganism is selected from the group consisting of *Bacillus natto* and *Bacillus subtilis*;
      (2) cultivating said inoculated microorganism, under aerating and agitating conditions, in a fermentation liquid medium, wherein said medium comprises rice bran, soybean, carbon, and water, and wherein the pH of the medium is about 7.5 to about 10; and
      (3) filtering the resultant cultivation broth, or an evaporation residue of said fermentation liquid, to obtain the fermentation composition.

5. The composition of claim 4, wherein said vitamin C is present in an amount of from about 1 to about 30 parts by weight, calculated as a solid content, per 100 parts by weight of the evaporation residue of said fermentation liquid.

6. The composition of claim 5, wherein said vitamin C is present in an amount of from about 10 to about 17 parts by weight, calculated as a solid content, per 100 parts by weight of the evaporation residue of said fermentation liquid.

7. The composition of claim 4, wherein the green tea extract is present in an amount of from about 1 to about 50 parts by weight, calculated as an evaporation residue, per 100 parts by weight of the evaporation residue of said fermentation liquid.

8. The composition of claim 7, wherein the green tea extract is present in an amount of from about 4 to about 25 parts by weight, calculated as an evaporation residue, per 100 parts by weight of the evaporation residue of said fermentation liquid.

9. The composition of claim 4, wherein the green tea extract is an extract selected from the group consisting of an ethanol extract and a water extract, and wherein the green tea extract is soluble in water.

10. A composition having superoxide dismutating activity comprising:
   (a) an extract of green tea or an evaporation residue of said green tea extract; and
   (b) a fermentation composition, wherein said fermentation composition is obtained by:
      (1) inoculating a microorganism on a culture medium, wherein said microorganism is selected from the group consisting of *Bacillus natto* and *Bacillus subtilis*.
      (2) cultivating said inoculated microorganism, under aerating and agitating conditions, in a fermentation liquid medium, wherein said medium comprises rice bran, soybean, carbon, and water, and wherein the pH of the medium is about 7.5 to about 10; and
      (3) filtering the resultant cultivation broth, or an evaporation residue of said fermentation liquid, to obtain the fermentation composition.

11. The composition of claim 10, wherein the green tea extract is present in an amount of from about 1 to about 50 parts by weight, calculated as an evaporation residue, per 100 parts by weight of the evaporation residue of said fermentation liquid.

12. The composition of claim 11, wherein the green tea extract is present in an amount of from about 4 to about 25 parts by weight, calculated as an evaporation residue, per 100 parts by weight of the evaporation residue of said fermentation liquid.

13. The composition of claim 10, wherein the green tea extract is an extract selected from the group consisting of an ethanol extract and a water extract, and wherein the green tea extract is soluble in water.

14. A method for treating hypertension comprising administering to a patient in need thereof a therapeutically effective amount of the composition of any of claims 10–13.

15. A method for treating constipation comprising administering to a patient in need thereof a therapeutically effective amount of the composition of any of claims 10–13 wherein the composition further comprises an oligosaccharide.

16. A composition as a treatment for constipation comprising a fermentation liquid obtained by:
   (a) inoculating a microorganism on a culture medium, wherein said microorganism is selected from the group consisting of *Bacillus natto* and *Bacillus subtilis*;
   (b) cultivating said inoculated microorganism, under aerating and agitating conditions, in a fermentation liquid medium, wherein said medium comprises rice bran, soybean, carbon, and water, and wherein the pH of the medium is about 7.5 to about 10; and
   (c) filtering the resultant cultivation broth, or an evaporation residue of said fermentation liquid, to obtain said fermentation liquid.

* * * * *